(12) United States Patent
Kent et al.

(10) Patent No.: US 11,020,287 B2
(45) Date of Patent: Jun. 1, 2021

(54) ARTICLE COMPRISING EMBEDDED CODE

(71) Applicant: The Procter & Gamble Company, Cincinnati, OH (US)

(72) Inventors: Jeffrey Michael Kent, Lebanon, OH (US); Taylor Javier Morris, Cincinnati, OH (US); John Andrew Strasemeier, Aurora, IN (US); Shahram Jahanian, Loveland, OH (US); Marita Susanna Hergert, Cincinnati, OH (US); Daniel Howard Hill, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 470 days.

(21) Appl. No.: 15/921,690

(22) Filed: Mar. 15, 2018

(65) Prior Publication Data
US 2018/0263832 A1    Sep. 20, 2018

Related U.S. Application Data

(60) Provisional application No. 62/472,913, filed on Mar. 17, 2017.

(51) Int. Cl.
| | |
|---|---|
| *A61F 13/84* | (2006.01) |
| *A61F 13/514* | (2006.01) |
| *A61F 13/511* | (2006.01) |
| *A61F 13/551* | (2006.01) |
| *G06Q 30/02* | (2012.01) |

(Continued)

(52) U.S. Cl.
CPC ...... *A61F 13/51496* (2013.01); *A61F 13/511* (2013.01); *A61F 13/514* (2013.01); *A61F 13/51394* (2013.01); *A61F 13/51498* (2013.01); *A61F 13/53* (2013.01); *A61F 13/551* (2013.01); *A61F 13/55105* (2013.01); *A61F 13/84* (2013.01); *G06Q 30/0282* (2013.01); *A61F 2013/8476* (2013.01); *A61F 2013/8497* (2013.01)

(58) Field of Classification Search
CPC .......... A61F 13/51394; A61F 13/51496; A61F 2013/8497; A61F 13/51; A61F 13/55105
See application file for complete search history.

(56) References Cited

U.S. PATENT DOCUMENTS

| | | |
|---|---|---|
| 3,465,350 A | 9/1969 | Keur et al. |
| 3,465,351 A | 9/1969 | Keur et al. |

(Continued)

FOREIGN PATENT DOCUMENTS

| | | |
|---|---|---|
| EP | 2843600 A1 | 3/2015 |
| WO | WO9400362 A1 | 1/1994 |

(Continued)

OTHER PUBLICATIONS

International Search Report, PCT/US2018/022529, dated Jul. 24, 2018, 16 pages.

*Primary Examiner* — Susan S Su
(74) *Attorney, Agent, or Firm* — Daniel S. Albrecht; Wednesday G. Shipp

(57) ABSTRACT

An absorbent article comprises a topsheet, a backsheet and an absorbent core disposed between the topsheet and backsheet; and a component comprising a base design, wherein the base design comprises one or more design elements and a camouflaged code.

15 Claims, 10 Drawing Sheets

(51) Int. Cl.
*A61F 13/53* (2006.01)
*A61F 13/513* (2006.01)

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,610,678 A | 9/1986 | Weisman et al. | |
| 4,662,875 A | 5/1987 | Hirotsu et al. | |
| 4,699,622 A | 10/1987 | Toussant et al. | |
| 4,846,815 A | 7/1989 | Scripps | |
| 4,892,536 A | 1/1990 | Desmarais et al. | |
| 4,894,060 A | 1/1990 | Nestegard | |
| 4,946,527 A | 8/1990 | Battrell | |
| 4,990,147 A | 2/1991 | Freeland | |
| 5,037,416 A | 8/1991 | Allen et al. | |
| 5,151,092 A | 2/1992 | Buell et al. | |
| 5,137,537 A | 8/1992 | Herron et al. | |
| 5,221,274 A | 6/1993 | Buell et al. | |
| 5,242,436 A | 9/1993 | Weil et al. | |
| 5,260,345 A | 11/1993 | Desmarais et al. | |
| 5,269,775 A | 12/1993 | Freeland et al. | |
| 5,387,207 A | 2/1995 | Dyer et al. | |
| 5,397,316 A | 3/1995 | LaVon et al. | |
| 5,499,978 A | 3/1996 | Buell et al. | |
| 5,507,736 A | 4/1996 | Clear et al. | |
| 5,549,791 A | 8/1996 | Herron et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,700,254 A | 12/1997 | McDowall et al. | |
| 5,865,823 A | 2/1999 | Curro | |
| 6,004,306 A | 12/1999 | Robles et al. | |
| 6,107,537 A | 8/2000 | Elder et al. | |
| 6,120,487 A | 9/2000 | Ashton | |
| 6,132,411 A | 10/2000 | Huber et al. | |
| 6,432,098 B1 | 8/2002 | Kline et al. | |
| 6,863,666 B2 | 3/2005 | Minato | |
| 7,435,243 B2 | 10/2008 | Miyamoto | |
| 7,786,341 B2 | 8/2010 | Schneider et al. | |
| 7,851,666 B2 | 12/2010 | Belau et al. | |
| 7,870,652 B2 | 1/2011 | Kline et al. | |
| 8,062,279 B2 | 11/2011 | Miyamoto | |
| 8,261,972 B2 | 9/2012 | Ziegler | |
| 8,382,736 B2 | 2/2013 | Kline et al. | |
| 8,690,852 B2 | 4/2014 | Macura et al. | |
| 8,939,957 B2 | 1/2015 | Raycheck et al. | |
| 8,979,815 B2 | 3/2015 | Roe et al. | |
| 8,992,499 B2 | 3/2015 | Kline et al. | |
| 9,060,904 B2 | 6/2015 | Hundorf et al. | |
| 9,072,634 B2 | 7/2015 | Hundorf et al. | |
| 9,211,356 B2 | 12/2015 | Gruenbacher et al. | |
| 9,220,640 B2 | 12/2015 | Ales et al. | |
| 9,358,161 B2 | 6/2016 | Lawson et al. | |
| 9,421,137 B2 | 8/2016 | LaVon et al. | |
| 2002/0016579 A1 | 2/2002 | Stenberg | |
| 2004/0246529 A1* | 12/2004 | Pruden | G06K 1/121 358/3.28 |
| 2007/0118087 A1 | 5/2007 | Flohr et al. | |
| 2007/0138286 A1* | 6/2007 | Kamijoh | G06K 19/06037 235/462.04 |
| 2007/0282286 A1* | 12/2007 | Collins | A61F 13/42 604/361 |
| 2008/0159798 A1* | 7/2008 | Culp | G06K 13/07 400/247 |
| 2008/0294134 A1* | 11/2008 | Schroer, Jr. | A61F 13/42 604/361 |
| 2008/0312622 A1 | 12/2008 | Hundorf et al. | |
| 2009/0221980 A1* | 9/2009 | Mosbacher | A61F 13/8405 604/385.01 |
| 2009/0247979 A1* | 10/2009 | Sosalla | A61F 13/49004 604/385.01 |
| 2010/0040826 A1 | 2/2010 | Autran et al. | |
| 2010/0055423 A1* | 3/2010 | Chretien | G06K 19/06046 428/209 |
| 2010/0300309 A1* | 12/2010 | Schneider | B65D 79/00 101/35 |
| 2011/0183712 A1* | 7/2011 | Eckstein | G06Q 30/016 455/556.1 |
| 2012/0172825 A1 | 7/2012 | Ales et al. | |
| 2012/0173249 A1 | 7/2012 | Popp et al. | |
| 2012/0316526 A1 | 12/2012 | Rosati et al. | |
| 2014/0074057 A1 | 3/2014 | Miyamoto | |
| 2014/0144579 A1 | 5/2014 | Brown et al. | |
| 2014/0148773 A1 | 5/2014 | Brown et al. | |
| 2014/0148774 A1 | 5/2014 | Brown et al. | |
| 2014/0228796 A1* | 8/2014 | Burvall | A61F 13/494 604/385.01 |
| 2014/0274642 A1 | 9/2014 | LaVon et al. | |
| 2014/0276525 A1 | 9/2014 | LaVon et al. | |
| 2015/0065973 A1 | 3/2015 | Roe et al. | |
| 2015/0066187 A1 | 3/2015 | Berg et al. | |
| 2015/0088088 A1 | 3/2015 | Wade et al. | |
| 2015/0126955 A1 | 5/2015 | Sauer et al. | |
| 2015/0230760 A1* | 8/2015 | Schneider | A61B 5/0015 600/300 |
| 2016/0175165 A1* | 6/2016 | Schneider | A61F 13/15804 604/385.3 |
| 2016/0206483 A1 | 7/2016 | Nishikawa et al. | |
| 2016/0270972 A1 | 9/2016 | Surushe et al. | |
| 2018/0271722 A1* | 9/2018 | Gonzalez Martinez | A61F 13/84 |

FOREIGN PATENT DOCUMENTS

| | | |
|---|---|---|
| WO | WO9510996 | 4/1995 |
| WO | WO9516746 A1 | 6/1995 |
| WO | WO9534329 | 12/1995 |
| WO | WO200059430 A1 | 10/2000 |
| WO | WO02067809 A2 | 9/2002 |
| WO | WO2012090087 A3 | 11/2012 |

* cited by examiner

ARTICLE COMPRISING EMBEDDED CODE

FIELD OF THE INVENTION

The present invention relates to articles comprising encoded information, especially absorbent articles comprising encoded information.

BACKGROUND OF THE INVENTION

Manufacturers of consumer products, such as absorbent articles, strive to provide optimal product performance along with consumer-desirable features. For instance with absorbent articles, absorbency and fit are balanced with comfort, softness and aesthetically pleasing designs.

In order to evaluate products, manufacturers often seek feedback from consumers and end users. Information may be provided on products themselves and/or packaging so that feedback may be correlated with the manufacturing details (e.g., the date of production, the line on which the product was produced, etc.). To date, this information has been provided in words, numbers, QR codes or other indicia that may distract from key characteristics as well as the overall appearance of the product and/or package. For example, the manufacturer may want to highlight the feel of the product or connote improved functionality through graphics or relative size of features. Yet, improper placement of manufacturing information could distract from said features that should be highlighted. For this reason, information is provided in limited locations and in limited space so as to minimize any distraction.

However, limiting the size and location where information is provided may lead to a failure to retrieve the information when obtaining feedback. Indeed, small print, inconspicuous placement and other complications may make it difficult for consumers to find or read the information. In addition, manufacturing information may be difficult to transmit via email, websites, mobile devices or other prevalent forms of communication. Further, consumers often have no incentive or prompt to engage with the manufacturer and provide the information. In such case, consumers may choose to select a different product without ever informing the manufacturer of an issue.

Therefore, there is a need for a means of incorporating manufacturing details into a product and/or package without distracting from product or package features. There is also a need for greater flexibility in how and where information is provided on a product or package. Likewise, there is a need for incorporating information in a manner that facilitates reacquisition of said information by the manufacturer. Further, it would be desirable to solve these issues in a cost-effective and efficient manner.

SUMMARY OF THE INVENTION

In some embodiments, an absorbent article includes a topsheet, a backsheet, an absorbent core disposed between the topsheet and backsheet; and a component comprising a base design, wherein the base design comprises one or more design elements and a camouflaged code.

In further embodiments, a package comprises a first absorbent article comprising a first code; a second absorbent article comprising a second code; wherein the first and second code differ by information contained in the code, one or more design elements, arrangement of design elements, number of design elements, interface capability and/or interface programs.

Additionally or alternatively, a package may comprise a first absorbent article comprising a first code and a second absorbent article comprising a second code. The first and second code differ by information contained in the code, one or more design elements, arrangement of design elements, number of design elements, interface capability and/or interface programs.

In certain embodiments, a package comprises a first code and a plurality of absorbent articles, wherein the first code comprises a camouflaged code and/or a digitally-interfacing code, and wherein the first code is provided on a surface of the package and/or on an insert in the package.

In further embodiments, an array of packages comprises absorbent articles. Each absorbent article comprises a topsheet, a backsheet and an absorbent core disposed between said topsheet and backsheet. The array comprises a first package comprising having a first code; and a second package comprising having a second code. The first and second code differ by information contained in the code, one or more design elements, arrangement of design elements, number of design elements, interface capability and/or interface programs.

DETAILED DESCRIPTION OF THE INVENTION

Figure 1:
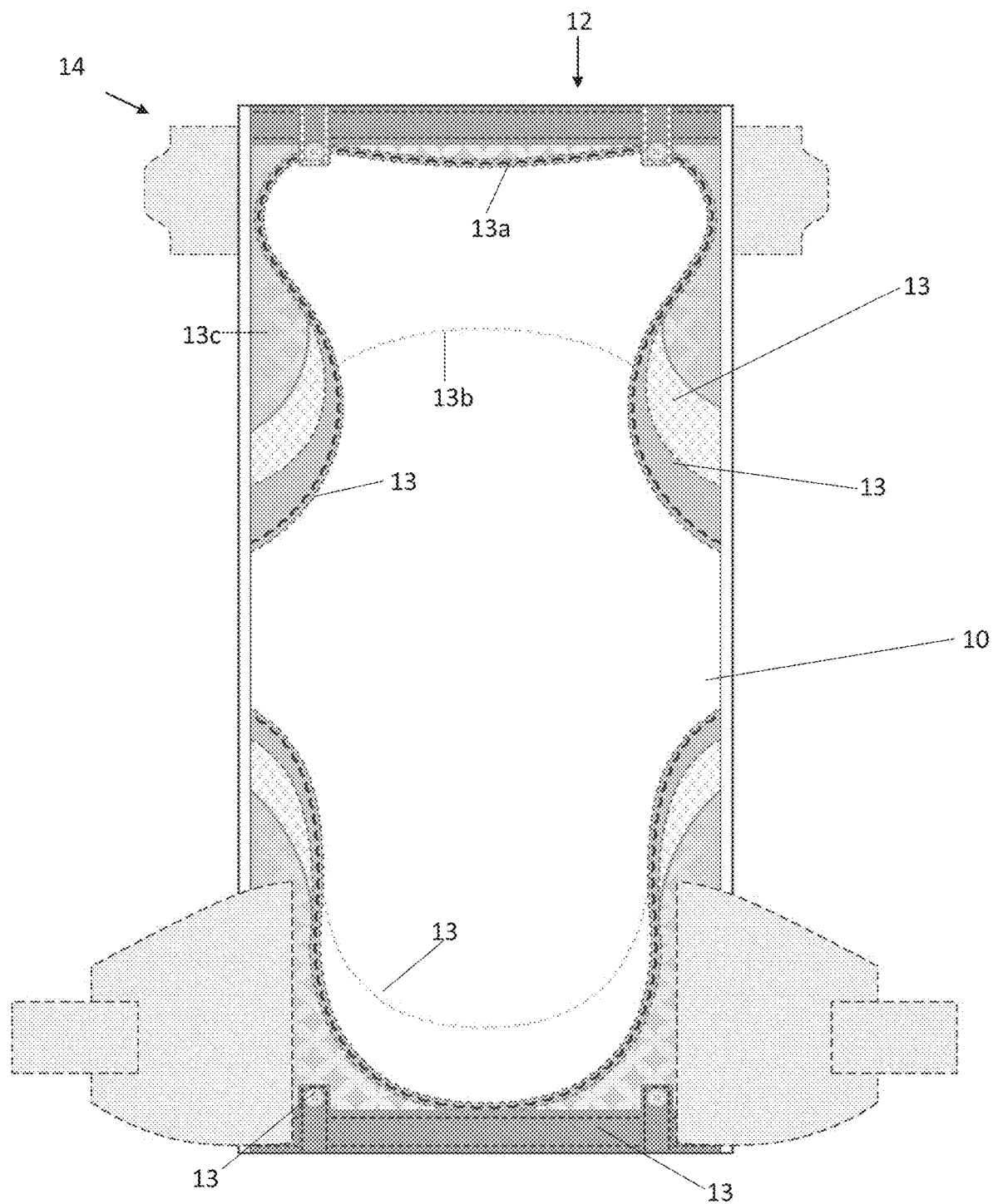
FIG. 1 is a schematic plan view of an exemplary embodiment of a product as detailed herein.

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Brand insignia" as used herein means objects, character representations, words, colors, shapes or other indicia that can be used to distinguish, identify or represent the manufacturer, retailer, distributor or brand of a product, including but not limited to trademarks, logos, emblems, symbols, designs, figures, fonts, lettering, crests or similar identifying marks.

"Camouflaged code" as used herein means a code is disguised or hidden in a base design and/or in one or a combination of design elements. A camouflaged code may be completely camouflaged (i.e., disguised or hidden in a base design or design element(s)) or partially camouflaged (i.e., portion of the code is hidden is disguised or hidden in the base design and/or one or more design elements).

"Code" as used herein means the presence, absence, or combination of one or more letters, numbers, shapes, objects, other symbols and/or indicia, which presence, absence or combination of letters, numbers, shapes, objects, other symbols and/or indicia represents information and is translatable into said information using one or more rules. Said rules may be defined before or at the time of generating the code. Encoded information as used herein means information represented by a code and determined by one or more rules.

"Consumer" as used herein means an individual who uses a product, and/or who purchases or otherwise procures a product for personal use or use by another. Consumer may include a parent, caregiver or other person who may apply an article to a wearer.

"Consumer-accessible program" as used herein means a software application that permits a product purchaser, product user or potential purchaser or user of a product to perform one or more functions or tasks using a computer (e.g., desktop, laptop, smartphone, tablet, mainframe, wearable technologies such as smartwatches). Nonlimiting examples of consumer-accessible programs include internet applications (e.g., MICROSOFT EDGE, GOOGLE CHROME, INTERNET EXPLORER, SAFARI), word processing applications, virtual and/or augmented reality applications (e.g., OCULUS RIFT, SAMSUNG GEAR VR, GOOGLE CARDBOARD), graphics applications (e.g., MICROSOFT PAINT, ADOBE PHOTOSHOP) and combinations thereof. In some embodiments, consumer-accessible programs permit an end-user to access and/or perform functions on one or more webpages.

"Design element" as used herein means a shape, text or combination of shapes and/or text that visually and/or tactilely create a distinct and discrete component. Design elements and/or combinations of design elements may comprise brand insignia. Design elements and/or combinations of design elements may comprise letters, words and/or graphics such as flowers, butterflies, hearts, character representations and the like. Design elements and/or combinations of design elements may comprise instructional indicia. Design elements may be textural and/or printed. Design elements can be formed by any suitable method including but not limited to printing, embossing, bonding, and combinations thereof.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Digitally-interfacing code" as used herein means a code is automatically discernable by one or more consumer-accessible programs. The digitally-interfacing code may be scannable and/or readable by a device and/or by a consumer-accessible program.

"Instructional indicia" as used herein means indicia that provides guidance or direction to a consumer or user. Nonlimiting examples include instructions regarding placement and/or fit of the article about the wearer, instructions regarding interfacing with a program, instructions regarding submitting information, and combinations thereof.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

Substrate Comprising Encoded Information

As shown in FIG. 1, a substrate 10 may comprise a base design 12, which may include one or more design elements 13. The substrate 10 may be part of a product 14, or in or on a package 1000 which contains the product. The substrate 10 may comprise a nonwoven, film, paper, label, sticker or combination thereof. The substrate 10 may in some nonlimiting examples comprise an adhesive on one or more sides, such that the substrate having the design 12 may be joined to another component. For instance, a substrate 10 may comprise an adhesive label such that the substrate having the design can be affixed to a package or product.

Figure 2:
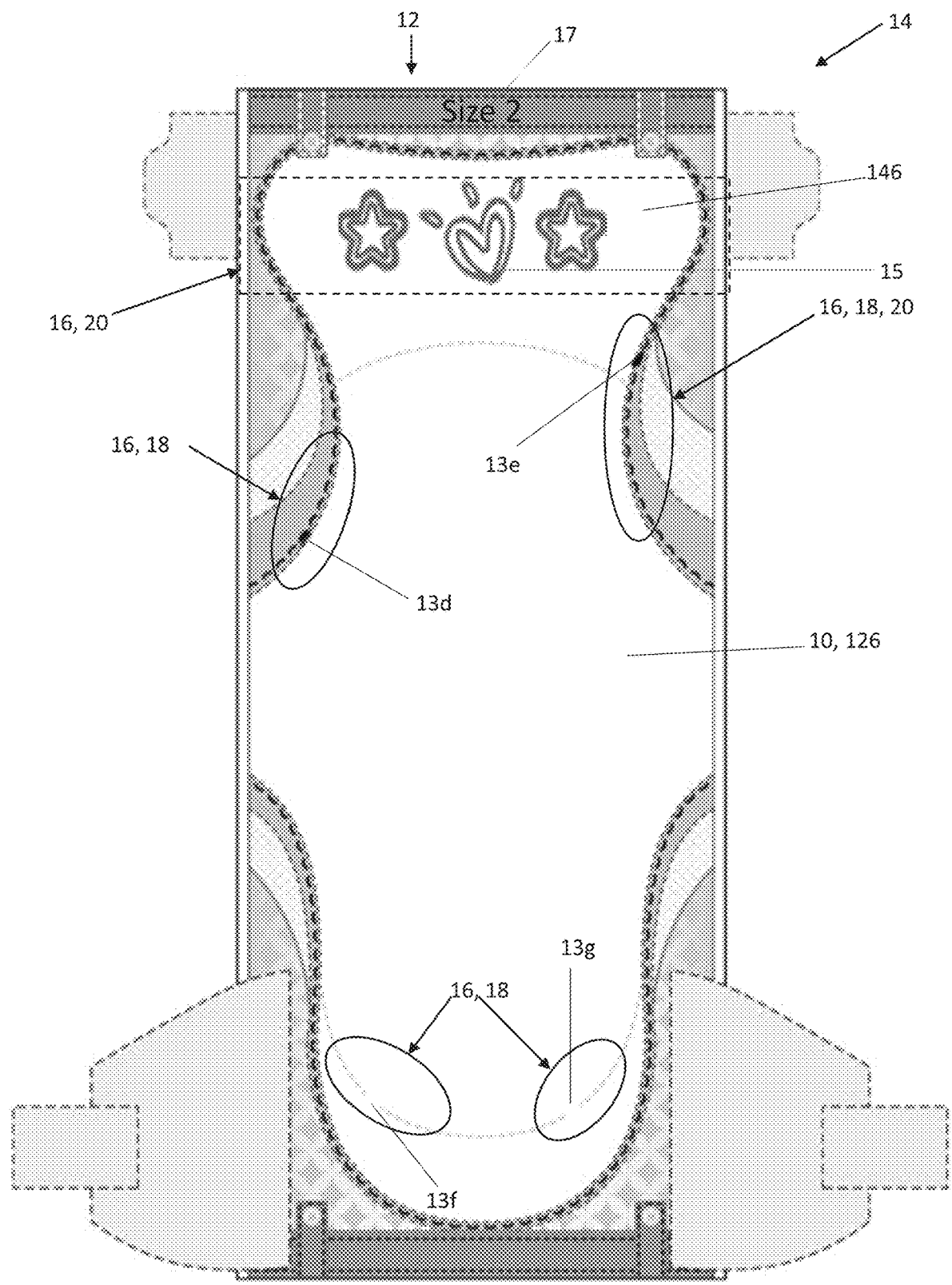
FIG. 2 is a schematic plan view of an exemplary embodiment of a product as detailed herein.

The base design 12 comprises an intentional design. In other words, the base design 12 is not merely a collection of lines, bars or other shapes intended solely to transmit information like a QR, RFID or bar code. Instead, the base design 12 provides an aesthetic quality to the substrate to enhance its appearance and/or feel. In certain embodiments, the base design includes graphics such flowers, butterflies, hearts, and/or character representations. The base design 12 may comprise brand insignia 15 and/or instructional indicia 17 as shown in FIG. 2. The base design 12 may comprise printing, texture(s), scent(s) or any combination thereof. Returning to FIG. 1, in some embodiments, two design elements 13a, 13b may be formed by different techniques. For example, a first design element 13a may comprise printing and a second design element 13b may comprise a texture, such as an embossment. In further embodiments, one design element 13 may be made by more than one technique. By way of nonlimiting example, a design element 13c may be formed by printing and embossing. Design elements may be formed by any suitable method including but not limited to printing, bonding, embossing, perforations, inclusion of fluid sensitive or temperature sensitive materials, light reflective materials, light absorptive materials, and/or patterned fluid coating (as disclosed in U.S. Pat. Pub. Nos., 2014/0148773, 2014/0148774 and 2014/0144579).

Turning to FIG. 2, the base design 12 may comprise one or more codes 16. The codes 16 in FIG. 2 are outlined by rectangles or ovals for ease of illustration.

A code 16 may represent information regarding a product 14. Nonlimiting examples of encoded information include the date, location, and/or process of manufacturing, the product retailer, storage facility(ies), shipment date, shipment means, raw materials used, inspectors and/or inspection processes, product features and/or configuration and combinations thereof. A code 16 may be deciphered by a rule or set of rules, which may be determined before or at the time of generating the code. The code 16 may provide a pictorial representation of product information. In this way, the code 16 may be communicated to a recipient (e.g., manufacturer, retailer) via an image, such as picture. Further, in certain embodiments, the code 16 may be communicated to a recipient through one or more programs as is discussed in more detail below.

Figure 3A:
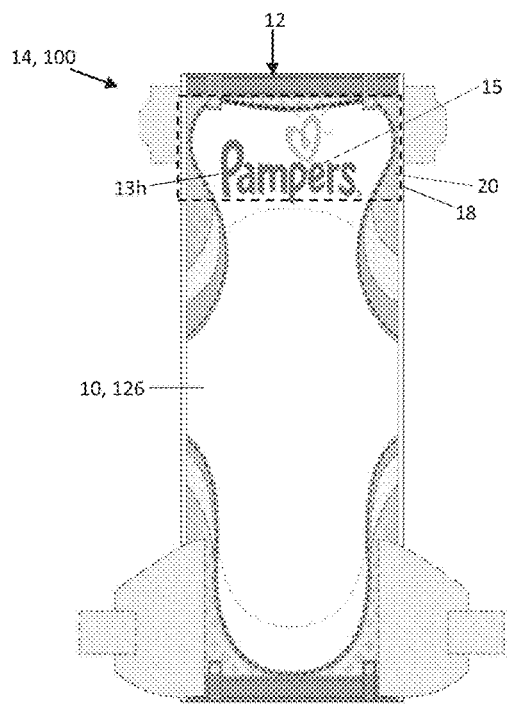
FIG. 3a-3c are schematic plan views of exemplary embodiments of products as detailed herein.
Figure 3B:
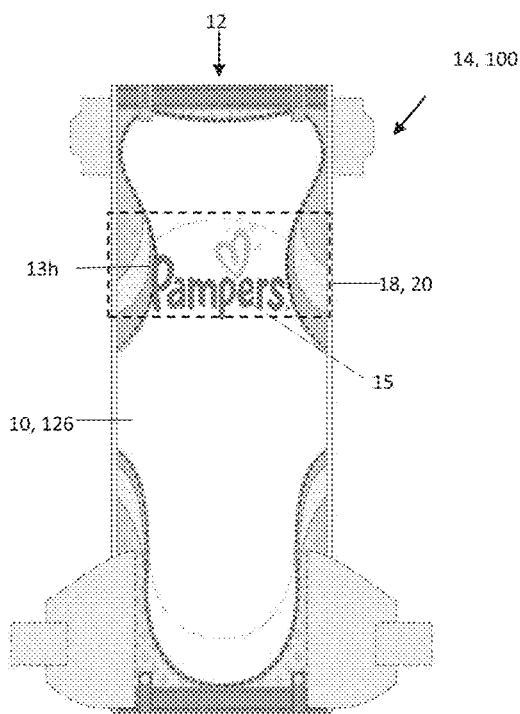
Figure 3C:
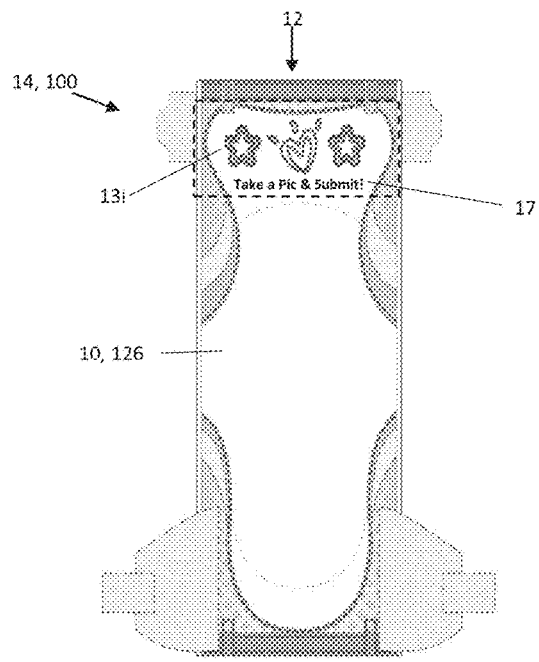

In some embodiments, the code 16 may comprise a camouflaged code 18. In certain embodiments, the camouflaged code 18 may be provided by modifying one or more design elements 13 in the base design 12. For example, in FIG. 2, two design elements 13d and 13e are darkened. The elements selected to be darkened may correlate with encoded information. For example, choosing the fifth element in the series could indicate the product was produced in May (i.e., the fifth month of the year), and choosing the fifteenth element in the series on the right side could indicate the product was produced in 2015. Additionally or alternatively, design elements may be added to the base design and/or design elements may be removed from the base design to correlate with encoded information. FIG. 2 illustrates gaps 13f, 13g between design elements; the placement of said gaps may correlate with encoded information. For example, the placement of said gaps could correlate with production location and/or production equipment. In certain embodiments, the code 16 may be provided by including particular texture(s) in the base design. By way of nonlimiting example, one or more design elements may be embossed to correlate with encoded information. In further embodiments, the code 16 may be provided by including scent(s) into the base design, wherein the scent correlates to encoded information. Additionally or alternatively, a code 16 may be provided by selecting one design element or combination of design elements among a number of choices. For instance, FIG. 3a illustrates a first selection of design elements 13h as outlined by a rectangle for ease of illustration, and FIG. 3c illustrates an alternative selection of design elements 13i (also outlined) in the same position. A code 16 may be provided by changing the position of one or more design elements (see FIGS. 3a and 3b), wherein the relative position may correlate to encoded information. Additional nonlimiting examples include modifying the color(s), texture, outline (e.g., solid line versus dotted line, thicker versus thinner line), and/or dimension(s) of one or more design elements to correlate to encoded information. In some nonlimiting examples, the color and/or background pattern of the substrate 10 may correlate to encoded information. In further nonlimiting examples, a design element changes colors in the presence of liquid and/or temperature changes. In such examples, a code 16 may be provided in the color that will appear after the change and/or in the color prior to the change.

Turning to FIGS. 3c-6, in certain embodiments, the code 16 is digitally-interfacing 20, such that it can be captured and/or deciphered by one or more consumer-accessible programs 22. Consumer-accessible programs 22 may be accessed and operated through devices 24 which can process data (also referred to hereinafter as computers), including but not limited to desktop computers, phones, tablets, wearable technologies such as smartwatches, and laptops. In some embodiments, the consumer-accessible program 22 comprises operating systems, programs operated locally on the device and/or programs requiring a connection to external networks such as internet applications.

In some embodiments, the substrate 10 may comprise instructional indicia 17. In nonlimiting examples, the instructional indicia may include prompts or indications of how to initiate the program and/or interface as can be seen in FIG. 3c, for example. It is also to be appreciated that the instructional indicia 17 may be included as part of a base design 12 without reference to a program and/or interfacing with a program.

Figure 4:
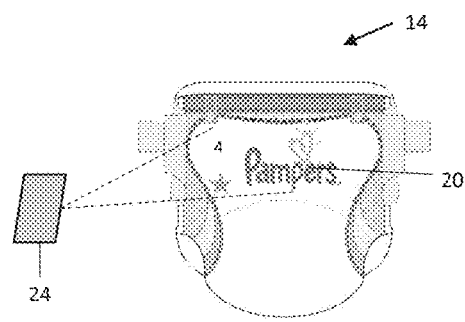
FIG. 4 is a schematic perspective view of an exemplary embodiment of a product and device as detailed herein.
Figure 5:
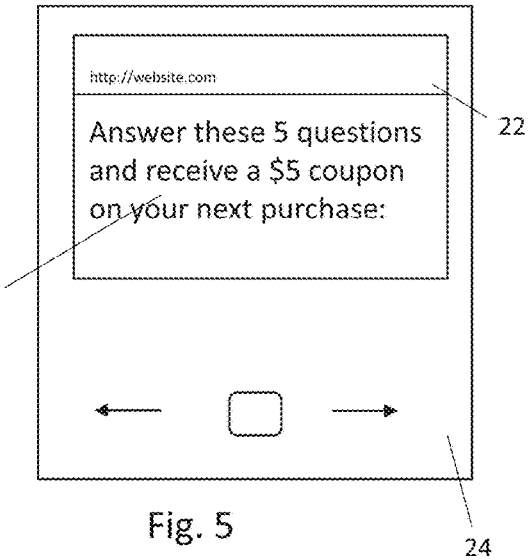
FIG. 5 is a schematic plan view of an exemplary embodiment of a device as detailed herein.
Figure 6:
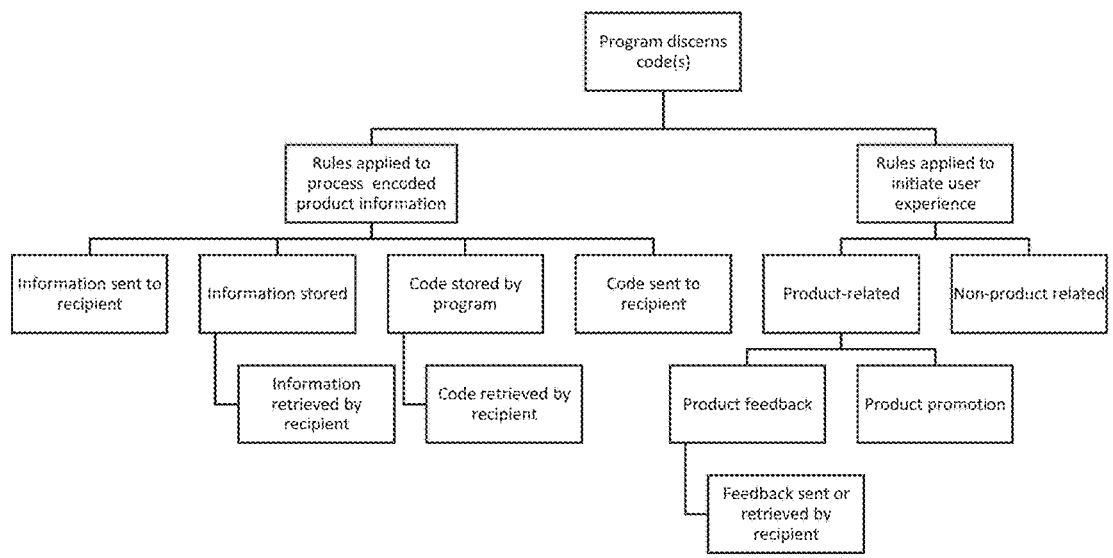
FIG. 6 is a schematic representation of an exemplary method for processing a code as detailed herein.

As shown in FIGS. 4-6, an individual may use a device 24 to transmit the code 20. In some embodiments, the user may initiate the interface by opening the program 22, and then submit the code 16. Alternatively, the individual may submit the code 16 to the device 24, and the submission can then trigger the program 22 to open. Submission of the code 16 may be accomplished by any suitable means. In some embodiments, a picture of the code 16 may be taken using the device. Said picture may be captured by or transferred to the program 22, or said picture may be converted into data that is captured by or transferred to the program. In other embodiments, the code 16 may be read by the device for a period of time sufficient for the device and/or program to capture the data without uploading and storing the image. In nonlimiting examples, the device 24 may register the code 16 from a distance of up to 36 inches, up to 24 inches, wherein the code is about 1 square inch or less, or about 0.75 square inches or less, or about 0.5 square inches or less. Known readable codes are not typically recognizable from at said distances. It is also to be appreciated that more than one piece of equipment may be necessary for processing the code. For instance, an individual may utilize a scanner to capture the code 16, and the scanner may transmit the image and/or underlying data to a computer on which the program is operating.

Once submitted to the program 22, the digitally-interfacing code 20 is automatically discernible by the program 22. In other words, the program 22 recognizes the elements, image, characters submitted as including the code 20 and/or as requiring processing of the code 16 using predetermined steps. For instance, the program 22 may automatically decipher the code 20 by applying rules and transmit the encoded information to an intended recipient (e.g., manufacturer, retailer, wholesaler, etc.). The program 22 may automatically transmit the code 16 (undeciphered) to an intended recipient. Additionally or alternatively, the program 22 may automatically store the code 16 or encoded information, and a recipient may retrieve said code or information from the program 22.

Once the code is submitted, the end user may be provided with a user experience 26. A user experience may be related to the product 14, including actions to promote the product 14 or other products and actions to solicit feedback concerning the product's features and/or performance. In certain embodiments, the user experience 26 may be unrelated to the product 14. Nonlimiting examples of user experiences 26 include games, coupon retrieval, reward points retrieval, surveys, videos, training on product use, augmented reality content, virtual reality content, advertisements, sales information, retrieval of product samples, product promotions, information sharing links, news and/or entertainment content, educational content or any combination thereof. In one nonlimiting example, the user experience 26 comprises a transformation of a static image into a moving or otherwise animated image (e.g., a static drawing turns into an animated cartoon, a still photo of a person becomes a video of person moving or speaking). In further nonlimiting examples, the user experience 26 comprises virtual and/or augmented reality content. For instance, actual items or images viewable through a device's camera may be modified within the program to include virtual features, including but not limited to people or items not actually present, animated characters, and/or movement or repositioning of items. In certain embodiments, the user experience 26 may comprise interactive content which may trigger additional content, such as voice command recognition, sending and receiving content such as pictures.

In some embodiments, the user experience 26 may be determined by the code 20. In other words, the program 22 may be programmed to respond to two different codes 20 with two differ user experiences 26 (e.g., one triggers a promotional coupon, one triggers a survey on product performance). The triggering of different experiences may correlate with any number of factors including but not limited to selected design elements 13, letters and/or numbers, brand insignia 15, colors, positioning of a design element, relative size of elements, the interaction of elements with background colors and/or patterns, and any combination thereof. As a nonlimiting example, FIGS. 3*a*-3*b* depict the same base design 12 with different positioning of a combination of design elements 13*h*. The combination of design elements and/or their positioning may constitute the code 20. A particular user experience 26 may be triggered the program's recognition of the relative position of two or more design elements. In the instant example, the code in FIG. 3*a* could trigger a different user experience than the code in FIG. 3*b*. As another nonlimiting example, FIG. 3*a* and FIG. 3*c* each have a collection of design elements 13*h*, 13*i* disposed in the same position on the substrate but the design elements are different. The differences in the design elements may trigger different user experiences. The program 22 may be instructed to respond to each potential code 20 according to interface rules. In certain embodiments, the interface rules may be modified dynamically. For instance, if a complaint is received about an article produced on Line X, on May 15, 2014, the program 22 can dynamically initiate a survey for all other users submitting codes 20 containing the same complete or partial manufacturing information. Dynamic adjustments can be made by providing program or device updates and/or by changing content delivered to the program.

In nonlimiting examples, digitally-interfacing codes 20 may also be camouflaged codes 18. In other nonlimiting examples, a digitally-interfacing code 20 is not camouflaged. In further nonlimiting examples, a digitally-interfacing code is partially camouflaged. In still further nonlimiting examples, a camouflaged code 18 is not digitally-interfacing.

Figure 7:
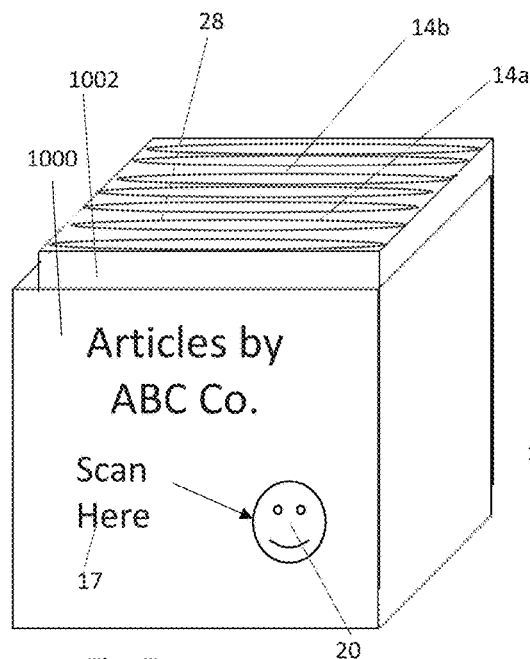
FIG. 7 is a schematic perspective view of an exemplary embodiment of a package as detailed herein.

In certain embodiments, a substrate 10 having a code 16 is incorporated into a product 14. Additionally or alternatively, a substrate 10 having a code 16 may form a portion of the package 1000 which comprises one or more products 14 as is shown in FIG. 7 for example. In some embodiments, products 14 are enclosed in external packaging 1000 and internal secondary packaging 1002 (e.g., individual product wrappers, internal bags for a plurality of products). Codes may be provided on external packages 1000 and/or secondary internal packages 1002. The codes on the outermost package 1000 may be the same or different as the codes on internal package 1002. A code may be applied directly to a substrate that forms a surface of the package 1000 and/or the code may be applied to a substrate that may be joined to the package surface by any suitable means, including but not limited to adhesive bonds and/or mechanical bonds. Descriptions herein related to including a code on a package 1000 apply equally to including a code on secondary package 10002.

Figure 9:
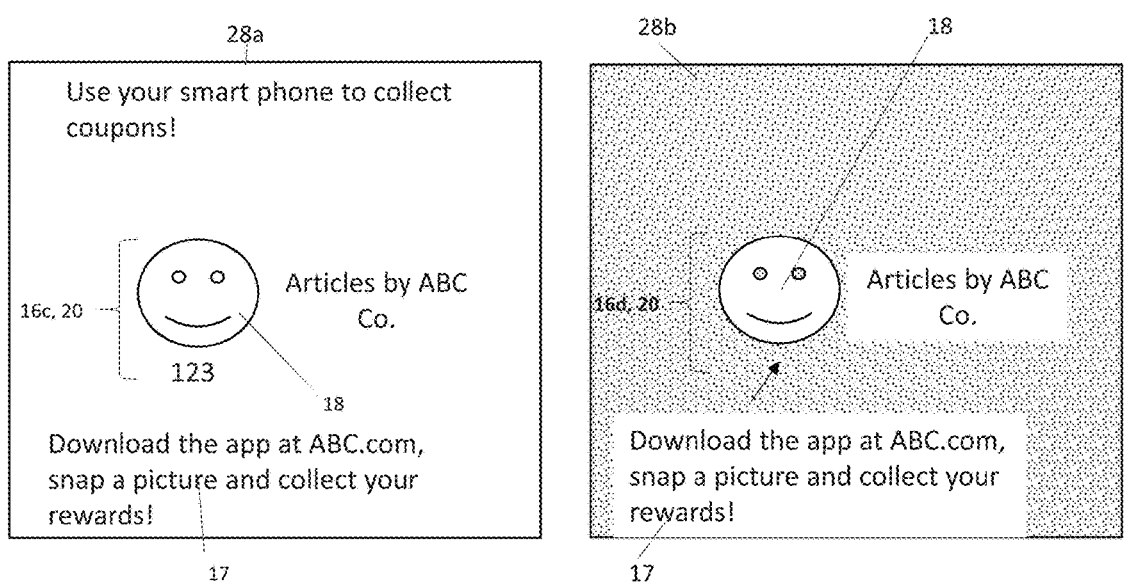
FIG. 9 is a schematic plan view of an exemplary embodiment of inserts as detailed herein.

Additionally or alternatively, a substrate having a code 16 is provided as an insert 28 in or on a package 1000 of products 14. Exemplary inserts 28 are shown in FIG. 9. Nonlimiting examples of inserts include cards, stickers, labels and combinations thereof. Inserts may be provided with an adhesive backing such that they may be affixed to packaging or products. Alternatively, inserts may be affixed to packaging or products by another suitable means. In some embodiments, inserts are provided without attachment to any product or package.

Package and Package Arrays

Figure 8:
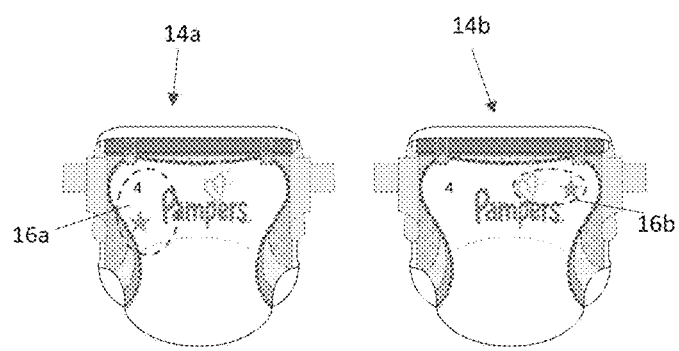
FIG. 8 is a schematic plan view of an exemplary embodiment of products as detailed herein.

In some embodiments, a package 1000 may comprise one or more products 14 as shown in FIGS. 7-8. (FIG. 7 schematically depicts a package comprising a first and second product. FIG. 8 schematically depicts the exemplary first and second products). In some embodiments, the package 1000 may comprise a first product 14*a*, such as a first absorbent article, and a second product 14*b*, such as a second absorbent article. The first product 14*a* may comprise a first code 16*a* and the second product may comprise a second code 16*b*, which is different than the first code 16*a*. The first code 16*a* and second code 16*b* may differ by any of the features described above with respect to creating a code. In some nonlimiting examples, the first code 16*a* and second code 16*b* may differ by the information contained in the code. For instance, the first code 16*a* and the second code 16*b* may indicate the first and second products 14*a*, 14*b* were completed at different times. Additional nonlimiting examples of difference in the codes 16*a*, 16*b* include differences in one or more design elements, the arrangement of design elements, the size and/or number of design elements, color and/or color changing capability, the code's respective ability to interface with a program 22, and/or the type of program 22 with which the respective code can interface. In certain embodiments, the first and second product 14*a*, 14*b* comprise the same base design 12 but for the changes associated with the respective codes 16*a*, 16*b*. Each code 16*a*, 16*b* may comprise a camouflaged code 18 and/or a digitally-interfacing code 20. In further embodiments, the package 1000 may comprise a plurality of products 14, wherein each product comprises a unique code 16. In some embodiments, the package 1000 may comprise a secondary package 1002 such that the products have an outermost package and a secondary internal package. It is to be appreciated that either or both of the outer package 1000 and secondary internal package 1002 may comprise codes as detailed herein. Where both comprise codes, the codes may be the same or different.

Additionally or alternatively, the package 1000 may comprise one or more inserts 28. In some embodiments, the package 1000 comprises an individually wrapped product and an insert in said wrapping. In further embodiments, the package 1000 comprises a plurality of products 14 as shown in FIG. 7 for example. The insert 28 may comprise a code 16 which provides encoded information about one or more products 14 in the package. In further nonlimiting examples, the package 1000 comprises a first insert 28a having a first insert code 16c, and a second insert 28b having a second insert code 16d as shown in FIG. 9. The first insert code 16c may comprise information relating to a first product 14a and the second insert code 16d may comprise information relating to a second product 14b. The first and second insert codes 16c, 16d may differ by any of the code features described above. In some nonlimiting examples, the first and second insert codes 16c, 16d may differ by the information contained in the codes. For instance, the first insert code 16c and the second insert code 16d may indicate that the respective products were inspected by different product inspectors. Additional nonlimiting examples of difference in the codes 16c, 16d include differences in one or more design elements, the arrangement of design elements, the size and/or number of design elements, color and/or color changing capability, the code's respective ability to interface with a program 22, and/or the type of program 22 with which the respective code can interface. In certain embodiments, the first and second inserts 28a, 28b comprise the same base design 12 but for the changes associated with the respective codes 16c, 16d. Each code 16c, 16d may comprise a camouflaged code 18 and/or a digitally-interfacing code 20. The package 1000 may further comprise one or more products 14 which comprise code(s). A code 16a on a product 14a may be the same or different from a code 16c on an insert 28a. It is also contemplated that a package 1000 may comprise one or more inserts 28 comprising codes 16 and a plurality of products that are each void of codes 16, or vice versa.

Figure 10:
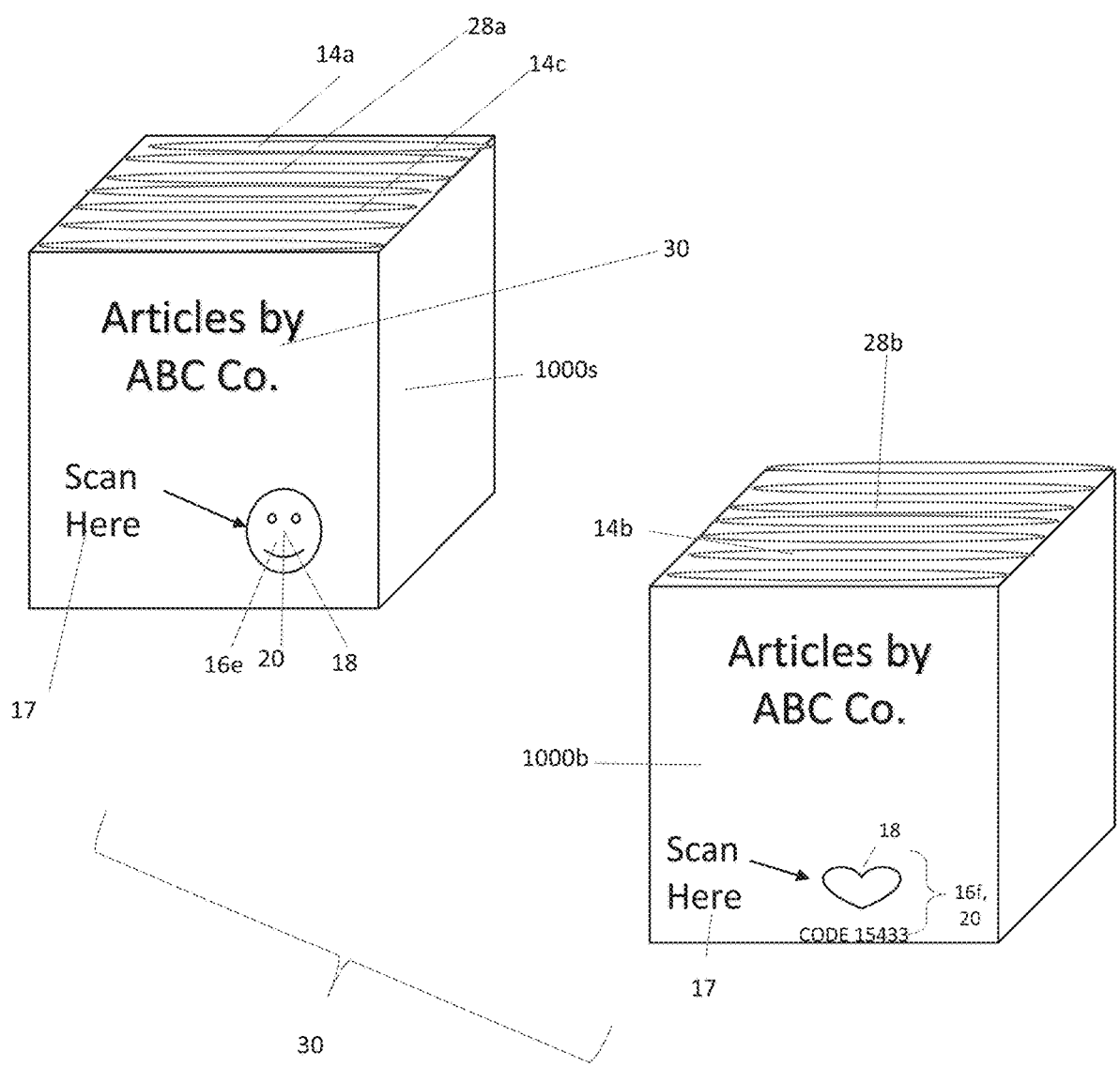
FIG. 10 is a schematic perspective view of an exemplary embodiment of an array of packages as detailed herein.

In another embodiment, an array 30 may comprise a first package 1000a and a second package 1000b as shown in FIG. 10. The first package 1000a may comprise a first product 14a having a first code 16a, and the second package 1000b may comprise a second product 14b having a second code 16b. For instance, the first package 1000a may comprise the exemplary first product 14a of FIG. 8, and the second package 1000b may comprise the exemplary second product 14b of FIG. 8. The first code 16a and second code 16b may differ by any of the code features described above. In some nonlimiting examples, the first code 16a and second code 16b may differ by the information contained in the code. For instance, the first code 16a and the second code 16b may indicate the first and second products 14a, 14b were produced at different locations. Additional nonlimiting examples of difference in the codes 16a, 16b include differences in one or more design elements, the arrangement of design elements, the size and/or number of design elements, color and/or color changing capability, the code's respective ability to interface with a program 22, and/or the type of program 22 with which the respective code can interface. In certain embodiments, the first and second product 14a, 14b comprise the same base design 12 but for the changes associated with the respective codes 16a, 16b. Each code 16a, 16b may comprise a camouflaged code 18 and/or a digitally-interfacing code 20. In further embodiments, at least one of the packages 1000a in the array 30 may comprise a plurality of products 14, wherein two or more products in said package 1000a comprise different codes. In other words, one of the packages may comprise a third product 14c which may comprise a code 16 that differs from the first and/or second code 16a, 16b.

Additionally or alternatively, the array 30 may comprise a first package 1000a comprising a first package code 16e and a plurality of products 14. The first package code 16e may comprise encoded information about one or more products 14a contained in the first package 1000a. The array 30 may further comprise a second package 1000b comprising a second package code 16f. The second package code 16f may comprise encoded information about one or more products 14b contained in the second package 1000b. The package codes 16e, 16f can be provided directly or indirectly on one or more surfaces of the respective packages as shown in FIG. 10. The first and second package codes 16e, 16f may differ by any of the code features described above. In some nonlimiting examples, the first and second package codes 16e, 16f may differ by the information contained in the codes. For instance, the first package code 16e and the second package code 16f may indicate the products in the respective packages were made on different production lines. Additional nonlimiting examples of difference in the codes 16e, 16f include differences in one or more design elements, the arrangement of design elements, the size and/or number of design elements, color and/or color changing capability, the code's respective ability to interface with a program 22, and/or the type of program 22 with which the respective code can interface. In certain embodiments, the first and second packages 1000a, 1000b comprise the same base design 12 but for the changes associated with the respective codes 16e, 16f. Each code 16e, 16f may comprise a camouflaged code 18 and/or a digitally-interfacing code 20. The first and/or the second package may comprise one or more products which comprise a code 16. A code on a product may be the same or different from a code on the package. It is also contemplated that a package 1000 may comprise one or more package code 16e and a plurality of products that are each void of codes 16, or vice versa. It is further contemplated that either package 1000a, 1000b may comprise secondary package(s) 1002, which may be provided with codes in the same manner as described above.

In certain embodiments, an array 30 includes a plurality of packages 1000a, 1000b, wherein each package comprises one or more inserts 28. Exemplary inserts 28a, 28b are shown in FIG. 9. In some nonlimiting examples, a first package 1000a comprises a first insert 28a having a first insert code 16c, and a second package 1000b comprises a second insert 28b having a second insert code 16d. The first insert code 28a may provide information related to one or more products 14a in the first package 1000a. The second insert code 28b may provide information related to one or more products 14b in the second package 1000b. The first and second insert codes may differ any code feature including those described above. In certain embodiments, the first and second inserts 28a, 28b comprise the same base design 12 but for the changes associated with the respective codes 16c, 16d. In further embodiments, at least one of the packages 1000a in the array 30 may comprise two or more inserts 28a, 28c, each having different codes. In other words, one of the packages may comprise a third product 14c and a third insert 28c may provide encoded information relating to said third product 14c. Each insert code 16 may comprise a camouflaged code 18 and/or a digitally-interfacing code 20. The first and/or the second package may comprise one or more products which comprise a code 16. A code on the products may be the same or different from a code on an insert. It is also contemplated that a package 1000 may comprise one or more insert codes 16c and a plurality of products that are void of codes 16, or vice versa.

Codes 16 may be provided to the manufacturer and may be used to modify future production as described, for example, in U.S. patent application Ser. No. 14/474,554. It is to be appreciated that codes may be used by manufacturers, retailers, producers, raw material suppliers and the like in the manner described herein.

Codes 16 may be formed on the substrate 10 by any suitable means, including but not limited to printing, embossing, bonding and combinations thereof. In some configurations, a substrate 10 is provided with a base design 12 and a design element comprising a code 16 is added thereto. In certain configurations, a substrate is provided with a series of codes 16 and subsequently separated into component portions of a series of products or packages or inserts, wherein each code in the series is provided on a separate product or package or insert. It is also contemplated that multiple codes may be provided on one product, package or insert.

Codes may be printed on a substrate using various printing methods, such as flexographic printing, rotogravure printing, screen-printing, inkjet printing, and the like. Suitable inks for printing include water-based, solvent-based, and energy curable inks. In certain embodiments, the ink is printed using inkjet printing. In some embodiments, design elements are provided using digital inkjet printing, which can be changed dynamically and thereby provide serialization of codes without significant downtime. Various inkjet printing processes are more particularly described in U.S. Pat. Nos. 3,465,350; 3,465,351; and 9,211,356.

In one embodiment, printing may be carried out by using cold laser printing technique. The mechanism for this cold laser printing is to provide an amount of energy by laser which will restructure molecule orders in a printing area so that the printing area will show different color to human eyes because of different diffuse reflection. According to this embodiment cold laser printing may be used to print, for example, codes 16 as disclosed herein, bar codes, and/or QR codes on to various substrates including plastic labels, polybags, cartons, or even on to glass bottles.

One advantage is that cold laser printing is more cost effective that alternative printing techniques or stickers. Another advantage is that cold laser printing enables individual codes, e.g. individual digitally-interfacing codes, to be printed onto to each substrate, polybag etc., for purposes such as anti-fraud, promotion, membership bonus and product production path tracking. The desirability of individual codes for each product has been described in EP-A-2 843 600, published on Mar. 4, 2015, incorporated herein by reference.

Articles Comprising the Substrate

Figure 11:
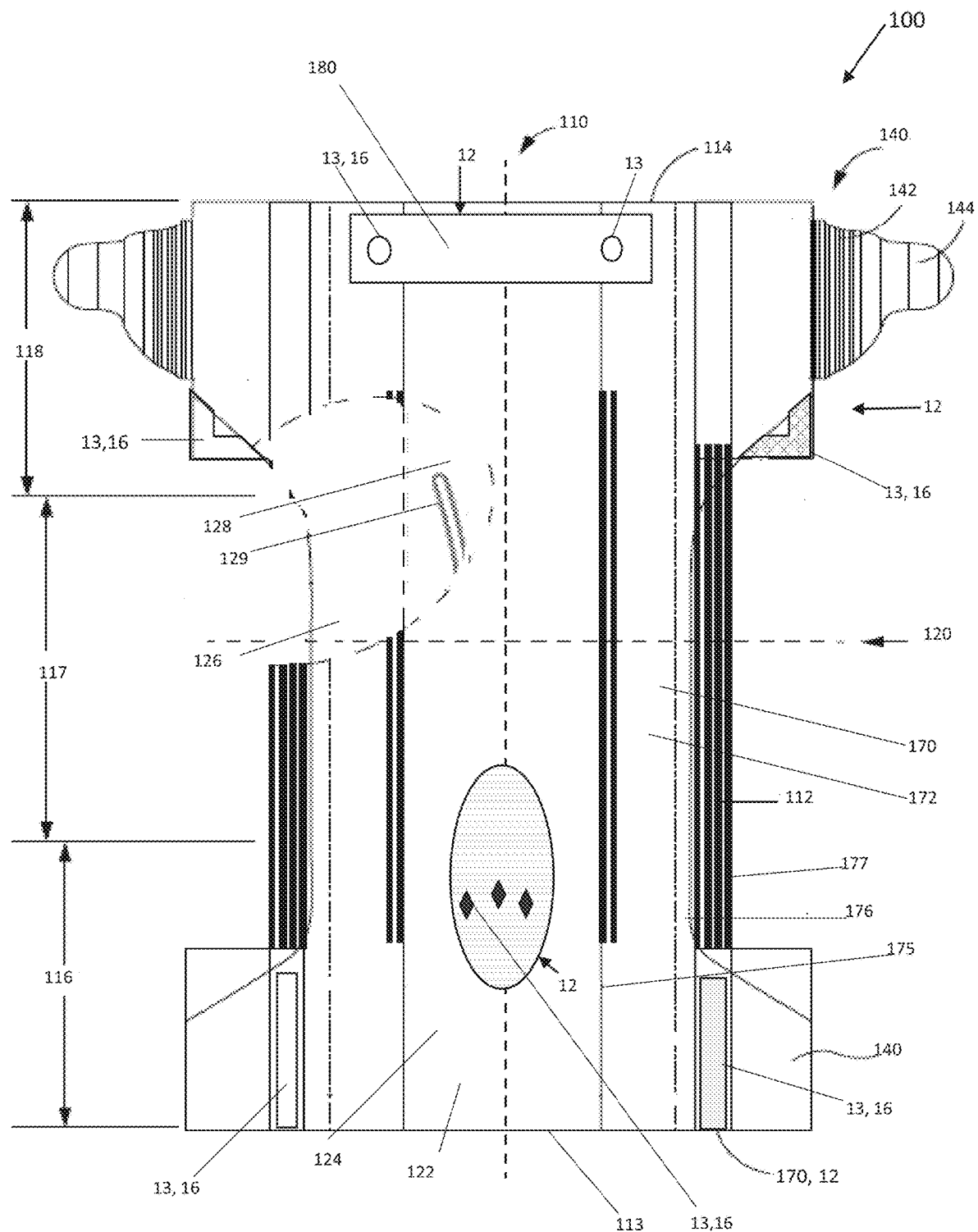
FIG. 11 is a schematic plan view of an exemplary embodiment of an absorbent article as detailed herein. The absorbent article is shown in a flat, uncontracted state.

The substrate 10 comprising the code 16 may be incorporated into product 14, such as an absorbent article 100. The absorbent article 100 may be disposable. FIG. 11 is a plan view of an exemplary, non-limiting embodiment of an absorbent article 100 of the present invention in a flat, uncontracted state. The body-facing surface of the absorbent article 100 is facing the viewer. The absorbent article 100 includes two longitudinal edges 112, a front waist edge 113 opposite a back waist edge 114, and a longitudinal centerline 110 and a lateral centerline 120. The absorbent article 100 comprises a chassis 122. The absorbent article 100 and chassis 122 are shown to have a first waist region 116, a second waist region 118 opposed to the first waist region 116, and a crotch region 117 located between the first waist region 116 and the second waist region 118. The waist regions 116 and 118 generally comprise those portions of the absorbent article 100 which, when worn, encircle the waist of the wearer. The crotch region 117 is the portion of the absorbent article 100 which, when the absorbent article 100 is worn, is generally positioned between the legs of the wearer.

The chassis 122 may comprise a liquid permeable topsheet 124, a backsheet 126, and an absorbent core 128 between the topsheet 124 and the backsheet 126. The topsheet 124 may be joined to the core 128 and/or the backsheet 126. The backsheet 126 may be joined to the core 128 and/or the topsheet 124. It should be recognized that other structures, elements, or substrates may be positioned between the core 128 and the topsheet 124 and/or backsheet 126, including but not limited to an acquisition-distribution system. In certain embodiments, the chassis 122 comprises the main structure of the absorbent article 100 with other features added to form the composite absorbent article structure. While the topsheet 124, the backsheet 126, and the absorbent core 128 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

The article 100 may comprise a component having the substrate 10 which comprises one or more codes 16. The substrate 10 may be disposed in one of the first waist region, second waist region, and/or crotch region. The substrate 10 may comprise a nonwoven, film or a combination thereof. Nonlimiting examples of components comprising the substrate include the topsheet 124, the backsheet 126, ADS 130, a leg cuff 172, an ear 140, a landing zone 146, a waist feature 180 and a belt 220. The codes 16 may be camouflaged codes 18 and/or digitally-interfacing codes 20.

Topsheet

The topsheet 124 may be positioned at least in partial contact or close proximity to a wearer. Suitable topsheets 124 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. In certain embodiments, the topsheet 124 comprises a nonwoven 14. In further embodiments, the topsheet 124 comprises a base design 12 having one or more codes 16. The base design may include graphics, instructional indicia, and/or brand insignia. The topsheet 124 is generally supple, soft feeling, and non-irritating to a wearer's skin. Generally, at least a portion of the topsheet 124 is liquid pervious, permitting liquid to readily penetrate through the thickness of the topsheet 124. One topsheet 124 useful herein is available from BBA Fiberweb, Brentwood, Tenn. as supplier code 055SLPV09U. The topsheet 124 may be apertured.

Any portion of the topsheet 124 may be coated with a lotion or skin care composition as is known in the art. Nonlimiting examples of suitable lotions include those described in U.S. Pat. Nos. 5,607,760; 5,609,587; 5,635,191; and 5,643,588. The specific examples are not limiting, as any lotion or skin care composition known in the art may be utilized. The topsheet 124 may be fully or partially elasticized or may be foreshortened so as to provide a void space between the topsheet 124 and the core 128. Exemplary structures including elasticized or foreshortened topsheets are described in more detail in U.S. Pat. Nos. 4,892,536; 4,990,147; 5,037,416; and 5,269,775.

Absorbent Core

Figure 12:
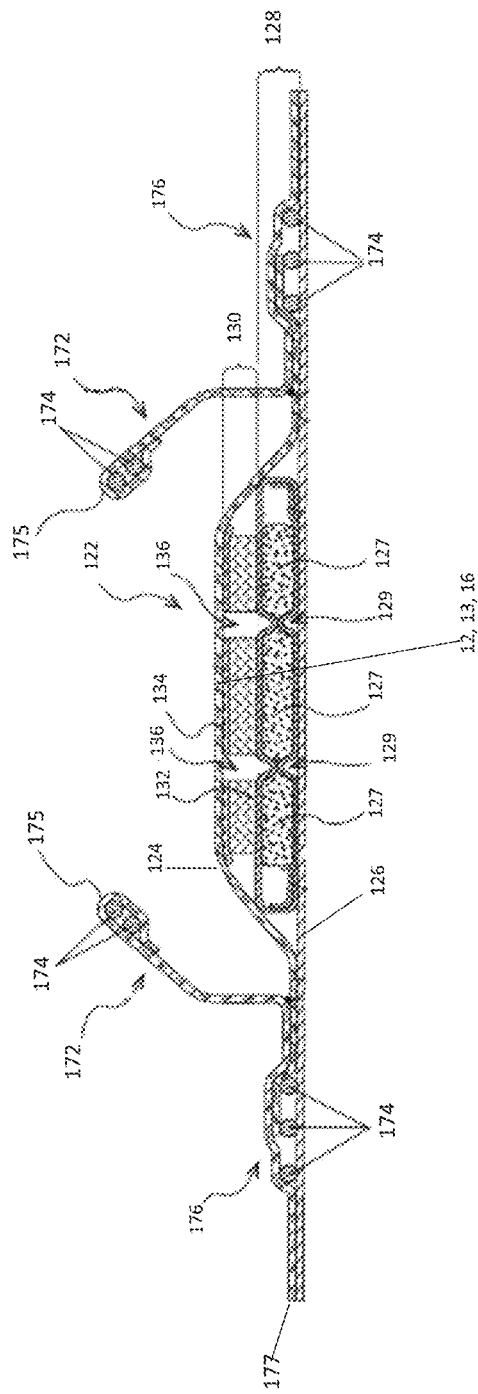
FIG. 12 is a cross-sectional view of the absorbent article taken about the lateral centerline in FIG. 11 in accordance with a non-limiting embodiment of the present invention.

As shown in FIG. 12, the absorbent core 128 may comprise a wide variety of liquid-absorbent materials 127 commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. The absorbent material 127 may be at least partially surrounded by a core wrap.

In some embodiments, the core may comprise one or more channels 129, which are substantially free of absorbent material. In one nonlimiting example, one or more channels may extend longitudinally.

Nonlimiting exemplary absorbent structures for use as the absorbent core 128 are described in U.S. Pat. Nos. 4,610,678; 5,260,345; 5,387,207; 5,397,316; 5,625,222; 8,979,815, 9,060,904, and 9,072,634; and U.S. patent application Ser. No. 13/491,642.

Backsheet

The backsheet 126 is generally positioned such that it may be at least a portion of the garment-facing surface of the absorbent article 100. Backsheet 126 may be designed to prevent the exudates absorbed by and contained within the absorbent article 20 from soiling articles that may contact the absorbent article 20, such as bed sheets and undergarments. The backsheet 126 is impervious to liquids. Suitable backsheet 126 materials include films such as those manufactured by Tredegar Industries Inc. of Terre Haute, Ind. and sold under the trade names X15306, X10962, and X10964. Other suitable backsheet 126 materials may include breathable materials that permit vapors to escape from the absorbent article 100 while still preventing exudates from passing through the backsheet 126. Exemplary breathable materials may include materials such as woven webs, nonwoven webs, polymeric films such as thermoplastic films of polyethylene or polypropylene, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 126 including, but not limited to, surface treatments, particular film selections and processing, particular filament selections and processing, etc. In one nonlimiting example, the backsheet is a thermoplastic film having a thickness of from about 0.012 mm to about 0.051 mm.

Backsheet 126 may also consist of more than one layer. The backsheet 126 may comprise an outer cover and an inner layer. The outer cover may be made of a non-woven material. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR.

In some embodiments, the backsheet 126 comprises a base design 12 and one or more codes 16, as shown for example in FIGS. 2-3c. The base design 12 may include graphics, instructional indicia and/or brand insignia.

While a variety of backsheet configurations are contemplated herein, it would be obvious to those skilled in the art that various other changes and modifications can be made without departing from the spirit and scope of the invention.

Acquisition-Distribution System (ADS)

Turning to FIG. 12, the absorbent article may comprise an ADS 130. One function of the ADS is to quickly acquire one or more of the fluids and distribute them to the absorbent core in an efficient manner. The ADS may comprise one, two or more layers, which may form a unitary layer or may remain as discrete layers which may be attached to each other. In certain embodiments, the ADS may be substantially free (e.g., 80%, 85%, 90%, 95%, or 99% free of) or completely free of SAP. In nonlimiting examples, the ADS may comprise a distribution layer 132 and/or an acquisition layer 134. In various embodiments, the acquisition layer 134 may acquire bodily exudates and the distribution layer 132 may distribute bodily exudates or both layers may distribute and/or acquire bodily exudates. An ADS disclosed herein may be positioned in an absorbent article: (1) intermediate a liquid pervious material or topsheet and an absorbent core; (2) intermediate an absorbent core and a liquid impervious material or backsheet; or may be otherwise located within the absorbent article. In an embodiment, more than one ADS may be provided in an absorbent article.

In a certain embodiment, the ADS may comprise chemically cross-linked cellulosic fibers. In nonlimiting examples, the distribution layer 132 may comprise at least 50%, or 60%, or 70%, or 80%, or 90%, or even up to 100%, by weight of the layer, of cross-linked cellulose fibers (including the cross-linking agents). The cross-linked cellulosic fibers may be crimped, twisted, or curled, or a combination thereof including crimped, twisted, and curled. Example chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an example cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. Example chemically cross-linked cellulosic fibers suitable for a distribution layer are disclosed in U.S. Pat. Nos. 5,549,791, 5,137,537, WO 9534329, or U.S. Pat. App. Publ. No. 2007/118087, U.S. Pat. Publ. No. 2008/0312622 A1.

The distribution layer may typically have an average basis weight of from 30 to 400 g/m² or from 100 to 300 g/m², specifically reciting all 1.0 g/m² increments within the above-specified ranges and any ranges formed therein or thereby. The density of the distribution layer may vary depending on the compression of the absorbent article, but may be between 0.03 to 0.15 g/cm³ or 0.08 to 0.10 g/cm³, specifically reciting all 1.0 g/cm³ increments within the above-specified ranges and any ranges formed therein or thereby, measured at 0.30 psi (2.07 kPa).

Additionally or alternatively, the ADS 130 may comprise an acquisition layer 134. In an embodiment, the acquisition layer 134 may be disposed, for example, between the distribution layer 132 and the topsheet 124. The acquisition layer 134 may comprise a nonwoven, such as an SMS or SMMS material, comprising a spunbond, a melt-blown and a further spunbond layer or alternatively a carded chemical-bonded nonwoven. In some embodiments, the acquisition layer 134 may comprise air or wet-laid cellulosic, cross-linked cellulosic, or synthetic fibers, or blends thereof. In certain embodiments, the acquisition layer 134 may comprise a roll-stock web of synthetic fibers (which may be processed to increase void space, such as by solid state formation), or a combination of synthetic and cellulosic fibers, bonded together to form a highloft material. Alternatively, the acquisition layer 134 may comprise absorbent open cell foam. The nonwoven material may be latex bonded. Example acquisition layers are disclosed in U.S. Pat. No. 7,786,341. Carded, resin-bonded nonwovens may be used, in particular where the fibers used are solid round or round hollow PET staple fibers (50/50 or 40/60 mix of 6 denier and 9 denier fibers). The acquisition layer 134 may be stabilized by a latex binder, for example a styrene-butadiene latex binder (SB latex).

A further acquisition layer may be used in addition to a first acquisition layer described above. For example, a tissue, nonwoven, or other layer may be placed between the first acquisition layer and the distribution layer. The tissue may have enhanced capillarity distribution properties compared to the acquisition layer described above. The tissue, nonwoven, or other layer and the first acquisition layer may be of the same size or may be of a different size. For example, the tissue, nonwoven, or other layer may extend further in the rear of the absorbent article than the first acquisition layer. An example of hydrophilic tissue is a 13-15 gsm high wet strength made of cellulose fibers from supplier Havix.

In some embodiments, one or more layers of the ADS may comprises channels 136. One or more of the channels 136 may be configured to work in concert with one or more channels 129 in the absorbent core 128, as discussed above. Furthermore, channels 136 may also provide increased void space to hold and distribute urine, feces or other body exudates within the absorbent article, leading to reduced leakage and skin contact.

In some embodiments, the ADS 130 comprises a base design having one or more codes 16. One or more design elements 13 may be provided in the form of printing which is visible through the topsheet. The base design 12 may include graphics, instructional indicia and/or brand insignia.

In nonlimiting examples, the acquisition layer 134 may comprise one or more codes 16.

Suitable ADS are described in WO 2000/59430, WO 95/10996, U.S. Pat. No. 5,700,254, WO 02/067809, and US Pat. Pub. No. 2015/065973 for example.

Ears/Fasteners:

The absorbent article 100 may include front ears and/or back ears 140 as shown in FIG. 11. The ears may be an integral part of the chassis, such as formed from the topsheet 124 and/or backsheet 126 as side panels. Alternatively, the ears may be separate elements attached by gluing, heat embossing, and/or pressure bonding. Each ear may be extensible or inextensible. The ears 140 may be formed from nonwoven webs, woven webs, knitted fabrics, polymeric and elastomeric films, apertured films, sponges, foams, scrims, and combinations and laminates thereof. In some embodiments, the ear may include elastomers (e.g., elastic strands, LYCRA® fibers), such that the ear is stretchable. In further embodiments, an ear 140 may comprise a base design 12 having one or more codes 16. The base design may include graphics, instructional indicia, and/or brand insignia as illustrated in FIG. 11.

The absorbent article 100 may also include a fastening system 142. When fastened, the fastening system 142 interconnects the first waist region 116 and the rear waist region 118 resulting in a waist circumference that may encircle the wearer during wear of the absorbent article 10. The fastening system 142 may comprise a fastener 144 such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 142 may also provide a means for holding the article in a disposal configuration as disclosed in U.S. Pat. No. 4,963,140. The fastening system 142 may also include primary and secondary fastening systems, as disclosed in U.S. Pat. No. 4,699,622. The fastening system 142 may be constructed to reduce shifting of overlapped portions or to improve fit as disclosed in U.S. Pat. Nos. 5,242,436; 5,499,978; 5,507,736; and 5,591,152. In some embodiments, the fastening system 142 and/or the fastener 144 is foldable. In further embodiments, the fastening system may comprise a base design 12 having one or more codes 16. The base design may include graphics, instructional indicia, and/or brand insignia.

Stretchable ears and/or fastening members may facilitate the attachment of the fastening members to a landing zone 146 and/or maintain the taped diapers in place around the wearer's waist. The landing zone 146 may be a portion of the backsheet 126, or may be a separate substrate 10, such as a nonwoven substrate 14, joined to the backsheet. In some embodiments, the landing zone 146 comprises a base design 12 having one or more codes 16 as is depicted in FIG. 2. The base design may include graphics, instructional indicia, and/or brand insignia.

Extensible ears and/or fastening members may provide a more comfortable and contouring fit by initially conformably fitting the absorbent article to the wearer and sustaining this fit throughout the time of wear well past when absorbent article has been loaded with fluids or other bodily exudates since the elasticized ears allow the sides of the absorbent article to expand and contract. Exemplary ears and/or fastening systems are disclosed in U.S. Pat. Nos. 6,863,666; 6,132,411; 7,870,652; 8,992,499; 8,690,852; 8,382,736.

Leg Gasketing System

As illustrated in FIGS. 11 and 12, the absorbent article 100 may comprise a leg gasketing system 170 attached to the chassis 122, which may comprise one or more cuffs. The leg gasketing system may comprise a pair of barrier leg cuffs 172. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge joined directly or indirectly to the topsheet 124 and/or the backsheet 126 and a free terminal edge 175, which is intended to contact and form a seal with the wearer's skin. In some embodiments, the free terminal edge 175 comprises a folded edge. The barrier leg cuffs 172 extend at least partially between the front waist edge 113 and the rear waist edge 114 of the absorbent article on opposite sides of the longitudinal axis 110 and are at least present in the crotch region. The barrier leg cuffs may be joined at the proximal edge with the chassis of the article by a bond which may be made by gluing, fusion bonding, or a combination of other suitable bonding processes.

The barrier leg cuffs may be integral with the topsheet 124 or the backsheet 126 or may be a separate material joined to the article's chassis. Each barrier leg cuff 172 may comprise one, two or more elastic elements 174 close to the free terminal edge 175 to provide a better seal. Additionally or alternatively, one or both of the barrier cuffs 172 may comprise a nonwoven 14. In some embodiments, a barrier leg cuff 172 comprises a base design 12 having one or more codes 16. The base design may include graphics, instructional indicia, and/or brand insignia.

In addition to the barrier leg cuffs 172, the article may comprise gasketing cuffs 176, which are joined to the chassis of the absorbent article, in particular to the topsheet 124 and/or the backsheet 126 and are placed externally relative to the barrier leg cuffs 172. The gasketing cuffs 176 may provide a better seal around the thighs of the wearer. A gasketing cuff may comprise a proximal edge and a free terminal edge 177. The free terminal edge 177 may comprise a folded edge. Each gasketing cuff may comprise one or more elastic elements 174 in the chassis of the absorbent article between the topsheet 124 and backsheet 126 in the area of the leg openings. Additionally or alternatively, one or both of the gasketing cuffs 176 may comprise a nonwoven 14. In some embodiments, a gasketing leg cuff 176 comprises a base design 12 having one or more codes 16. The base design may include graphics, instructional indicia, and/or brand insignia.

All, or a portion of, the barrier leg cuffs and/or gasketing cuffs may be treated with a lotion or another skin care composition. In further embodiments, the leg gasketing system comprises barrier leg cuffs that are integral with gasketing cuffs.

Suitable leg gasketing systems which may be part of the absorbent article are disclosed in U.S. Pat. App. No. 62/134, 622, Ser. No. 14/077,708; U.S. Pat. Nos. 8,939,957; 3,860, 003; 7,435,243; 8,062,279.

Waist Feature

The absorbent article 100 may comprise at least one elastic waist feature 180 that helps to provide improved fit and containment, as shown in FIG. 11. The elastic waist feature 180 is generally intended to expand and contract to dynamically fit the wearer's waist. Elasticized waist features 180 include waistbands, waist cuffs having pockets formed from a portion of the waist feature 180 that is unattached from the chassis 122, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 180 may be joined to the chassis 122 in the first waist region 116 and/or in the second waist region 118. In some embodiments, a waist feature 180 comprises a base design 12 having one or more codes 16. The base design may include graphics, instructional indicia, and/or brand insignia. In some embodiment, the waist feature 180 comprises a belt 220, in particular a belt on an absorbent pant.

Adult or Baby Pant Absorbent Articles

Figure 13B:
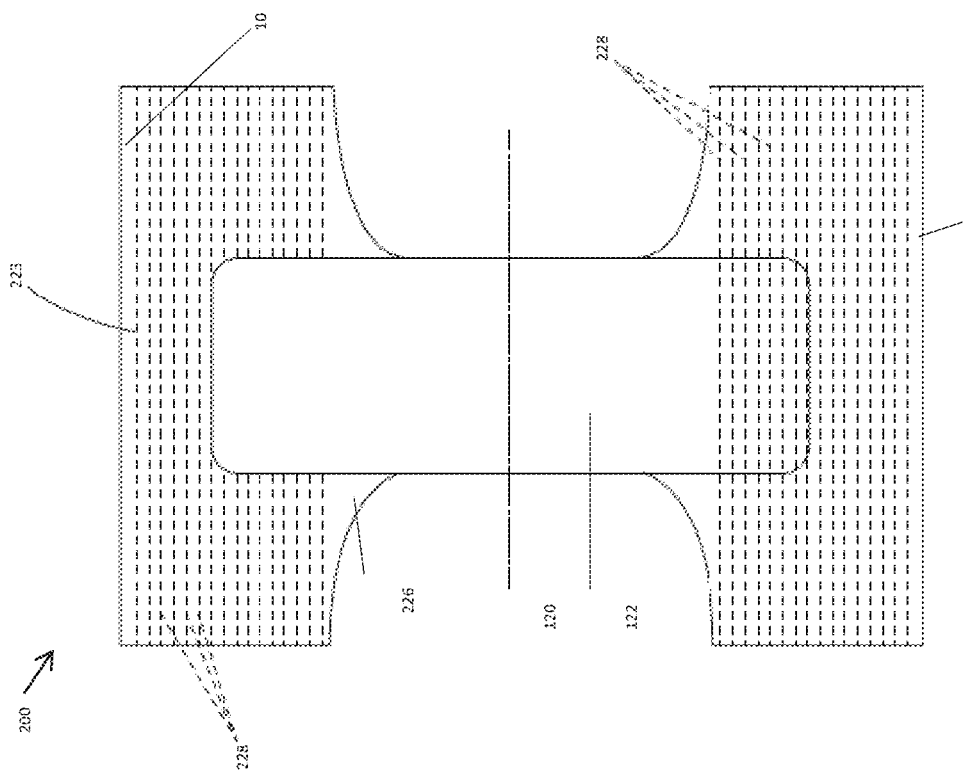
FIG. 13b is a schematic plan view of an exemplary embodiment of an absorbent pant precursor structure, prior to joining of the front and rear sections of the belt.
Figure 13A:
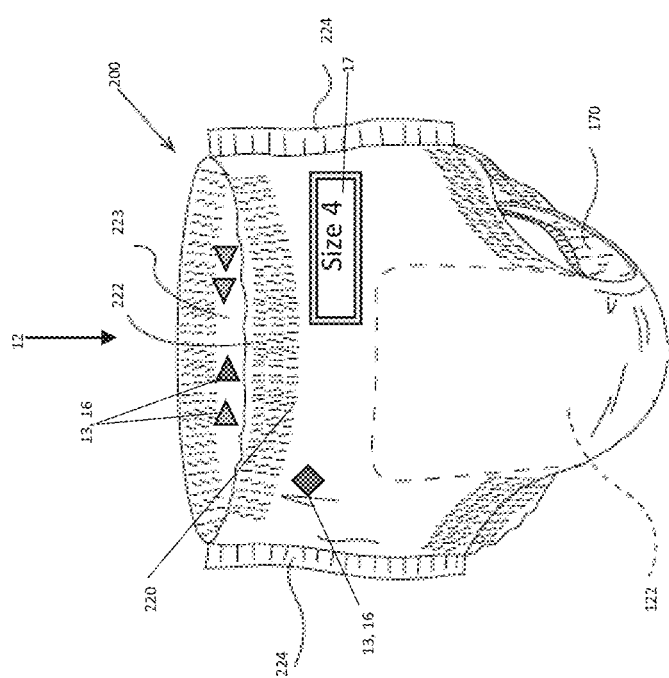
FIG. 13a is a schematic perspective view of an exemplary embodiment of an absorbent pant as detailed herein.

In some embodiments, the article 100 may comprise an absorbent pant 200 as shown in FIGS. 13a-13b. The absorbent pant may comprise include a chassis 122, a belt 220 to be positioned about the wearer's waist, and optionally a leg gasketing system 170. FIG. 13b depicts an exemplary precursor structure of the pant in FIG. 13a, in an open configuration laid out flat and stretched out laterally against elastic-induced contraction. In the final assembly of the pant, the front belt portion 222 is joined to rear belt portion 223 at seams 224, which may be permanent or refastenable. To form the pant 200, the precursor structure may be folded at or about lateral centerline 120 with the topsheet 124 facing inward, and the longitudinal edges of the front 222 and rear 223 belt portions may be joined at seams 224, forming a pant structure having leg openings, front waist edge and rear waist edge. In this way, the pant 200 may comprises a pre-formed, continuous waist opening and pre-formed, continuous leg openings for the wearer at the time of donning the pant 200.

The front and rear belt portions 222, 223 may be the outermost structures forming the front and rear regions of a pant 200. The pant may include an outer wrap 226 wrapping the entirety of the front, crotch and rear regions, and forming an outermost pant-shaped structure. In some embodiments, the outer cover of the backsheet forms the outer wrap. Additional layer(s) and elastic members 228 to form front and rear belt portions 222, 223 may be disposed to the inside of outer wrap 226, and be suitably affixed thereto by adhesive lamination, bonding or any other suitable mechanism. An outer wrap 226 may be formed of one or more sections of nonwoven web and may be cut to a profile providing suitably tailored leg opening edge profiles as desired.

Waist features, such as belt portions, may further comprise one or more elastic members 228. The elastic members 228 may be elastomeric fibers, such as LYCRA® fibers available from INVISTA of Wichita, Kans., in various decitex levels. The elastic members 228 may also comprise any heat shrinkable elastic material as is well known in the art. Other suitable elastics can be made various other materials including but not limited to: rubbers, styrene ethylbutylene styrene, styrene ethylene propylene styrene, styrene ethylene propylene styrene, styrene butadiene styrene, styrene isoprene styrene, polyolefin elastomers, elastomeric polyurethanes, and other elastomeric materials known in the art, and combinations thereof. In some nonlimiting examples, the elastic members may be extruded strand elastics with any number of strands (or filaments). In some embodiments, the elastic members can have a decitex ranging from 50 to 2000, or any integer value for any decitex value in this range. However, the skilled person may select the appropriate decitex based on the desired contraction and other principles discussed herein. In further embodiments, the elastic members may be in a form of film. Examples of films have been described in prior patent applications (see, for example, U.S. Pat. App. Pub. No. 2010/0040826). The film may be created with a variety of resins combined in at least one of several sublayers, the latter providing different benefits to the film.

In addition, elastic members 228 may take a multitude of configurations. For example, the width may be varied; a single strand or several parallel or non-parallel strands of elastic material may be used; or a variety of shapes may be used including rectilinear and curvilinear; or a variety of cross sectional shapes can be used (circular, rectangular, square, etc.).

Layers of a waist feature (e.g., belt portion) and/or chassis 122 may be joined together about elastic strands 228 by adhesive deposited between the layers, by thermal bonds, by compression bonds, or by a combination thereof. In other examples, the one or more elastic members may be strips or a section of film formed of elastomeric material. Where the elastic member is elongate, it may be desirable that the longer dimension be laterally oriented, or even substantially aligned with the lateral direction, as strands 228 are depicted in FIG. 13b for example.

A belt portion or other form of waist feature may comprise at least 3 waist elastic members 228, at least 5 elastic members 228, at least 10 waist elastic members 228, or at least 15 waist elastic members 228, or from about 2 to about 35 waist elastic members, or from about 5 to about 25 waist elastic members, reciting for each range every 1 increment therein.

Side seams 224 may be permanent or refastenable. Permanent seams may be formed between the front belt portion and the rear belt portion by any bonding mechanism wherein the front and rear belt portions may not be forcibly separated without substantial damage to one or both of the front and rear belt portions, or without any included mechanism by which substantial reattachment or refastening may be effected. Bonding forming permanent seams may include compression bonding, thermal bonding/welds, ultrasonic bonding or adhesive bonding. Refastenable seams may be formed between the front belt portion and the rear belt portion by any mechanism configured to permit substantially non-destructive forcible separation of the front and rear belt portions, and subsequent substantial reattachment or refastening at the same locations. One example of such mechanism is a hook-and-loop fastening system, for example, a VELCRO fastening system. A suitably sized and shaped hooks component may be bonded to one of the front or rear belt portions along the longitudinal edges thereof, and a suitably sized and shaped loops component may be bonded to the other of the front or rear belt portions along the longitudinal edges thereof, in positions in which they may be brought together and engaged to form seams 224. Examples are depicted in U.S. Pat. App. Ser. Nos. 61/787, 416; 61/787,332; 61/666,065.

Exemplary belt and absorbent pant constructions are disclosed in U.S. patent application Ser. Nos. 14/598,783 and 14/032,595.

In some embodiments, the belt 220 and/or outer cover 226 may comprise a base design 12 having one or more codes 16. The base design may include graphics, instructional indicia, and/or brand insignia.

Package

The absorbent articles 100 of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 14:
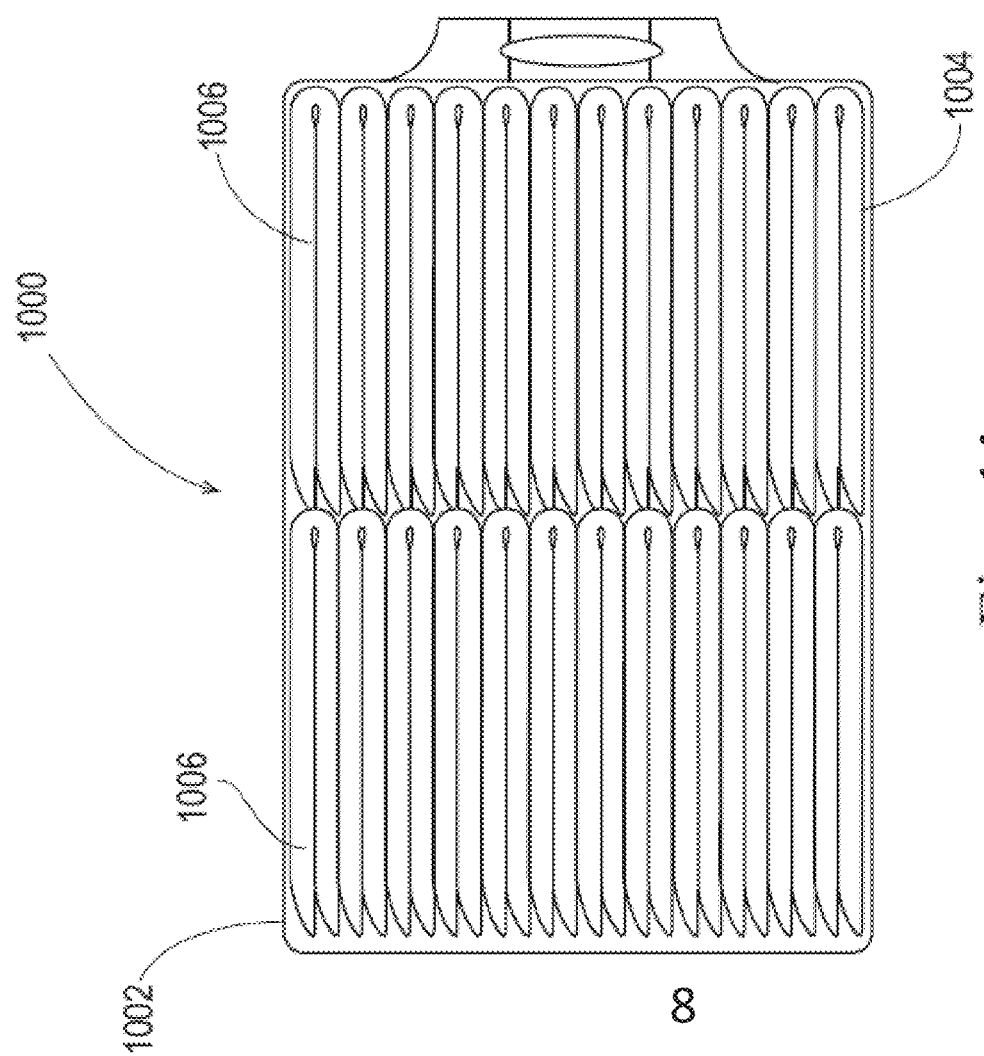
FIG. 14 is a schematic perspective view of an exemplary embodiment of a package as detailed herein.

FIG. 14 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Combinations

A. A package comprising a plurality of absorbent articles having a first absorbent article, and a first base design having a first code wherein the first code comprises a camouflaged code and/or a digitally-interfacing code, and wherein the first code comprises encoded information relating to the first absorbent article.

B. A package according to paragraph A wherein the first base design is provided on a first item selected from the group consisting of the first absorbent article, a surface the package, a secondary package, and an insert.

C. A package according to paragraphs A or B wherein the first item comprises the first absorbent article, wherein the first absorbent article comprises a topsheet, a backsheet and an absorbent core disposed between the topsheet and backsheet, and wherein the first code is disposed on the backsheet, a leg cuff, an ear, the topsheet, an acquisition layer, or a fastening element.

D. A package according to any of the preceding paragraphs wherein the first code comprises a camouflaged code.

E. A package according to paragraph D wherein the camouflaged code comprises a texture, wherein the texture corresponds to the encoded information.

F. A package according to paragraphs D or E wherein the camouflaged code comprises a scent which corresponds to encoded information.

G. A package according to any of the preceding paragraphs wherein the base design comprises at least one design element which corresponds to encoded information.

H. A package according to paragraph G wherein the at least one design element comprises a color and/or dimension that corresponds to encoded information.
I. A package according to any of the preceding paragraphs wherein the first base design comprises a graphic, instruction indicia, brand insignia or combinations thereof.
J. A package according to any of the preceding paragraphs wherein the first code comprises a digitally-interfacing code, wherein the digital-interfacing code communicates with a consumer-accessible program, and wherein the consumer-accessible program initiates a user experience.
K. A package according to paragraph J wherein the user experience comprises a virtual reality and/or augmented reality experience.
L. A package according to paragraphs J or K wherein the consumer-accessible program is accessible through a computer.
M. A package according to any paragraphs J-L wherein the digital-interfacing code communicates the encoded information to the consumer-accessible program.
N. A package according to any of the preceding paragraphs comprising a second base design having a second code wherein the first and second code differ by information contained in the code, one or more design elements, arrangement of design elements, number of design elements, interface capability and/or interface programs, wherein the second code comprises a camouflaged code and/or a digitally interfacing code, and wherein the second code comprises encoded information relating to a second absorbent article.
O. A package according to any of the preceding paragraphs wherein the second base design is disposed on a second item selected from the group consisting of the second absorbent article, the surface the package, the secondary package, and an insert, wherein the second item differs from the first item.
P. An array of packages comprising a package according to any of the preceding claims and a second package, wherein the second package comprises a third absorbent article, a third base design having a third code and wherein the third code of the second package relates to the third absorbent article;
  wherein the third code is provided on a third item selected from the group comprising the third absorbent article, a surface of the second package, a secondary package with the second package, and an insert within the second package;
  and wherein the third code differs from the first code by information contained in the codes, one or more design elements, arrangement design elements, number of design elements, interface capability and/or interface programs.
Q. The package according to any of the preceding claims wherein two or more base designs are the same except for differences in their respective codes.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
  a topsheet, a backsheet and an absorbent core disposed between the topsheet and backsheet; and
  a component comprising a base design, wherein the base design comprises a plurality of design elements and a digitally interfacing camouflaged code;
  wherein the camouflaged code is at least partially formed from one of the plurality of design elements of the base design; and
  wherein the camouflaged code is not a QR code, RFID code, or bar code.

2. The absorbent article of claim 1 wherein the camouflaged code comprises a texture, wherein the texture corresponds to encoded information.

3. The absorbent article of claim 1 wherein the base design comprises a graphic.

4. The absorbent article of claim 1 wherein at least one of the plurality of design elements corresponds to encoded information.

5. The absorbent article of claim 4 wherein the at least one of the plurality of design elements is capable of changing colors.

6. The absorbent article of claim 4 wherein the at least one of the plurality of design elements comprises a color and/or dimension that corresponds to encoded information.

7. The absorbent article of claim 1 wherein the camouflaged code comprises a scent which corresponds to encoded information.

8. The absorbent article of claim 1 wherein the component comprises the backsheet, a leg cuff, an ear, the topsheet, an acquisition layer, or a fastening element.

9. The absorbent article of claim 1 wherein the digitally interfacing camouflaged code communicates with a consumer-accessible program, and wherein the consumer-accessible program initiates a user experience.

10. The absorbent article of claim 9 wherein the user experience comprises a virtual reality and/or augmented reality experience.

11. The absorbent article of claim 9 wherein the digitally interfacing camouflaged code communicates encoded product information to the consumer-accessible program.

12. The absorbent article of claim 9 wherein the consumer-accessible program is accessible through a computer.

13. A package comprising:
  the absorbent article of claim 1;
  wherein the package comprises a package code.

14. The package of claim 13, wherein the package code comprises a camouflaged code.

15. The package of claim 13 wherein the package code is a digitally interfacing code that communicates with a consumer-accessible program.

\* \* \* \* \*